US006264916B1

(12) United States Patent
Ranganathan et al.

(10) Patent No.: US 6,264,916 B1
(45) Date of Patent: Jul. 24, 2001

(54) N,N-DIMETHYLDIATRIZOIC ACID AND ITS CONJUGATES AS HEPATOBILIARY AGENTS FOR X-RAY CT IMAGING

(75) Inventors: Rama S. Ranganathan, Princeton; Thangavel Arunachalam, Plainsboro; Michael F. Tweedle, Princeton, all of NJ (US)

(73) Assignee: Bracco Research, USA, NJ (US)

( * ) Notice: Subject to any disclaimer, the term of this patent is extended or adjusted under 35 U.S.C. 154(b) by 0 days.

(21) Appl. No.: 09/484,840

(22) Filed: Jan. 18, 2000

Related U.S. Application Data

(62) Division of application No. 09/273,522, filed on Mar. 22, 1999, now Pat. No. 6,051,210, which is a continuation of application No. 08/856,796, filed on May 15, 1997, now abandoned.

(51) Int. Cl.[7] .................................................... A61K 49/04

(52) U.S. Cl. ....................... 424/9.453; 424/9.4; 424/9.45; 424/9.1; 424/1.65; 424/1.11

(58) Field of Search .................................. 424/1.11, 1.65, 424/9.1, 9.3, 9.4, 9.5, 9.42, 9.45, 9.453, 9.455, 9.6, 9.7, 9.8

(56) References Cited

U.S. PATENT DOCUMENTS

| | | | |
|---|---|---|---|
| 2,611,786 | 9/1952 | Wallingford . | |
| 3,178,473 | 4/1965 | Holterman et al. . | |
| 3,701,771 | 10/1972 | Almen et al. . | |
| 3,825,591 | 7/1974 | Felder et al. . | |
| 3,883,535 | 5/1975 | Felder et al. . | |
| 4,192,859 | 3/1980 | Mackaness . | |
| 4,364,921 | 12/1982 | Speck et al. . | |
| 4,396,598 | 8/1983 | Lin . | |
| 4,607,123 * | 8/1986 | Schuster et al. | 564/153 |
| 4,735,795 | 4/1988 | Robinson et al. . | |
| 5,019,370 | 5/1991 | Jay et al. . | |
| 5,310,537 | 5/1994 | Illig et al. . | |
| 6,051,210 * | 4/2000 | Ranganathan et al. | 424/9.455 |

OTHER PUBLICATIONS

H. Suter and H. Zutter, Helv. Chim. Acta, 54, 255–2559 (1971), Röntgen–Kontrastmittel.

* cited by examiner

*Primary Examiner*—Dameron L. Jones
(74) *Attorney, Agent, or Firm*—Irme Balogh

(57) ABSTRACT

Compounds having formulae I, II or/III, or pharmaceutically acceptable salts thereof,

I

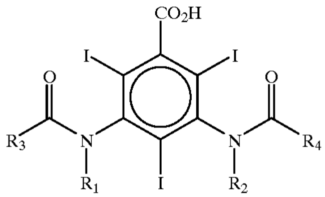

II

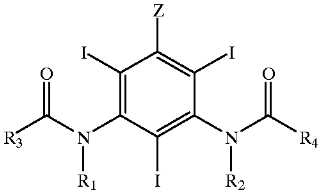

III

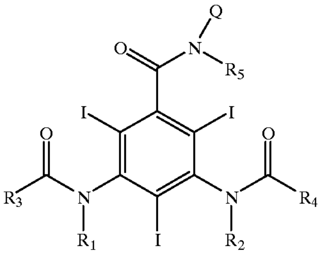

wherein

Z is 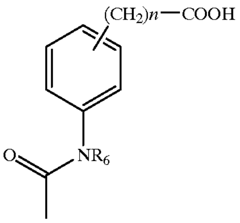 ,

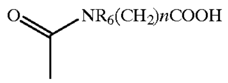 or

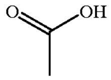

;

Q is 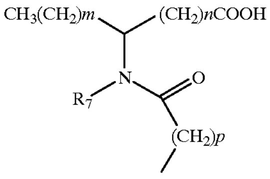 or

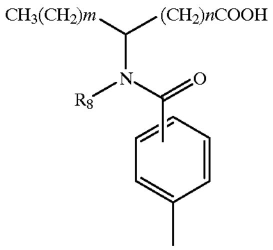

;

$R_1$, $R_2$, $R_3$, $R_4$, $R_5$, $R_6$, $R_7$ and $R_8$ are the same or different and are hydrogen, alkyl, substituted or unsubstituted cycloalkyl, substituted or unsubstituted aralkyl, substituted or unsubstituted aryl, haloalkyl, hydroxyalkyl, alkoxyalkyl, carboxyalkyl or carboxamido alkyl with the proviso that in formula I $R_2$ and $R_3$ cannot be methyl; and m, n and p are the same or different and are 0–24 with the proviso that $m+n \leqq 24$, are useful as contrast agents in x-ray imaging compositions and methods.

26 Claims, No Drawings

N,N-DIMETHYLDIATRIZOIC ACID AND ITS CONJUGATES AS HEPATOBILIARY AGENTS FOR X-RAY CT IMAGING

This application is a divisional of application Ser. No. 09/273,522 filed on Mar. 22, 1999, now U.S. Pat. No. 6,051,210 which in turn is a continuation of application Ser. No. 08/856,796 filed on May 15, 1997 now abandoned.

BACKGROUND OF THE INVENTION

1. Filed of the Invention

This invention relates to compositions containing conjugates of N,N-dimethyldiatrizoic acid and methods for their use in diagnostic radiology. More particularly, the invention relates to compositions containing N,N-dimethyldiatrizoic acid or a conjugate thereof for use as hepatobiliary agents for x-ray CT imaging.

2. Reported Developments Roentgenographic examination utilizing X-rays and computed tomography (hereinafter CT) scans of fractures and other conditions associated with the skeletal system is routinely practiced without the use of contrast agents. X-ray visualization of organs containing soft tissues, such as the gastrointestinal tract, heart, lung, kidneys and spleen, requires the use of contrast agents which attenuate x-ray radiation. D. P. Swanson et al. in "Pharmaceuticals In Medical Imaging", 1990, MacMillan Publishing Company, provides an excellent background in medical imaging utilizing contrast agents and compositions therewith.

Roentgenographic examination of the GI tract are indicated for conditions of digestive disorders, changes in bowel habit, abdominal pain, GI bleeding and the like. Prior to radiological examination, administration of a radiopaque contrast medium is necessary to permit adequate delineation of the respective lumen or mucosal surface from surrounding soft tissues. Accordingly, a contrast medium is administered orally to visualize the mouth, pharynx, esophagus, stomach, duodenum and proximal small intestine. The contrast medium is administered rectally for examination of the distal small intestine and the colon.

The most widely used contrast agent for the visualization of the GI tract is barium sulfate administered as a suspension orally or rectally as an enema. (See, for example, U.S. Pat. Nos. 2,659,690; 2,680,089; 3,216,900; 3,235,462; 4,038, 379; and 4,120,946.) Notwithstanding its relatively good contrast characteristics, negligible absorption from the GI tract following oral or rectal administration and speedy excretion form the body, barium sulfate has certain disadvantages. In the presence of intestinal fluids it lacks homogeneity and poorly adheres to mucus membranes which can result in poor x-ray images. In the colon, when administered as an enema, it flocculates and forms irregular clumps with fecal matter.

In addition to, or in place of barium sulfate, iodinated organic compounds have also been used as GI contrast agents since the iodine atom is an effective x-ray absorber. They have the most versatility and are utilized in the widest variety of procedures. They are very absorptive of x-rays with which the iodine interacts and produce a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agents can be utilized. (For iodinated agents see, for example, U.S. Pat. Nos.: 2,786,055; 3,795,698; 2,820,814; 3,360,436; 3,574,718; 3,733,397; 4,735,795; 5,047,228; 5,308,607; 5,310,538; 5,318,769; 5,334,370; 5,336,484 and 5,344,638.)

The desiderata for an ideal GI contrast agent includes: good toxicological profile; the ability to fill the entire bowel/lumen and evenly coat the gut mucosa so that the presence of the bowel is detectable when the lumen is not distended; nonirritation to the intestinal mucosa; and passage through the GI tract without producing artifacts or stimulating vigorous intestinal peristalsis.

We have found that the compounds of the present invention having these and other desirable characteristics in the GI tract do satisfy the requirements of an x-ray contrast agent when incorporated in suitable aqueous oral or rectal formulations for examination of the GI tract utilizing x-rays and CT scans.

During extensive investigation we have also discovered that the compounds of the present invention are eminently suitable for intravenous administration for CT imaging of organs, such as the kidneys and liver. It is well known by those skilled in the art that agents for intravenous administration must meet certain requirements that arc more stringent than the requirements for oral and rectal administration since the agents are directly introduced into the blood stream of the patient. The imagining of the organ or body section is accomplished by means of roentgenography commonly referred to as computed tomography (CT) or computerized axial tomography (CAT) in which the emergent x-ray beam is measured by a scintillation counter, the electronic impulses are recorded on a magnetic disk, and then processed by a computer for reconstruction display.

SUMMARY OF THE INVENTION

In one aspect the present invention provides hepatobiliary agents for x-ray CT imaging having the formula I, II or III, or a pharmaceutically acceptable salt thereof:

I

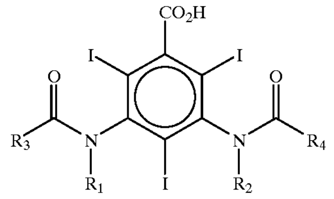

II

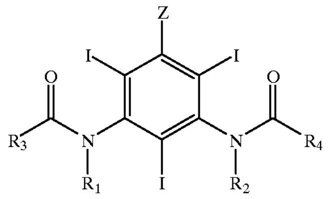

III

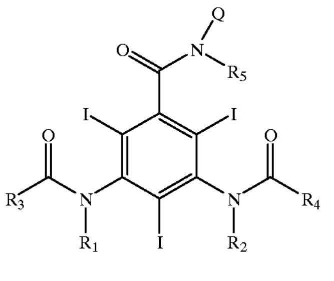

-continued wherein

Z is

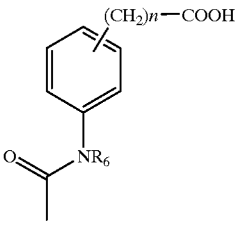

,

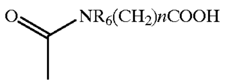

or

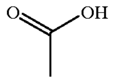

;

Q is

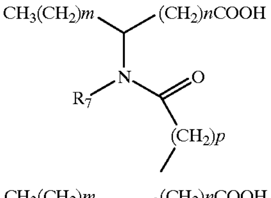

or

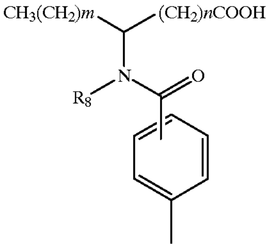

;

$R_1$, $R_2$, $R_3$, $R_4$, $R_5$, $R_6$, $R_7$ and $R_8$ are the same or different and are hydrogen, alkyl, cycloalkyl, aralkyl, aryl, haloalkyl, hydroxyalkyl, alkoxyalkyl, carboxyalkyl or carboxamido alkyl; and m, n and p are the same or different and are 0–24 with the proviso that $m+n\leqq 24$.

The terms herein throughout the specification and the claims have the following meaning.

The term “alkyl” refers to both straight, and branched, unsubstituted chains of 1 to 10 carbon atoms. Those chains having 1 to 5 carbon atoms are preferred. Methyl is the most preferred alkyl group.

The term “cycloalkyl” refers to cyclic hydrocarbon groups of 3 to 7 carbon atoms. The groups may be unsubstituted or substituted by, for example, alkyl, halogen, hydroxy, hydroxyalkyl, alkoxy, alkanoyl, alkanoyloxy, amino, alkylamino, dialkylamino, alkanoylamino, thiol, alkylthiol, nitro, cyano, carboxy, carbamoyl, alkoxycarbonyl, alkylsulfonyl, sulfonamido and the like.

The term “aryl” refers to phenyl, pyridyl, furanyl, thiophenyl, pyrrolyl, imidazolyl and the like, all of which may be substituted. Preferred substituted aryl groups are those substituted with 1, 2 or 3 halogen, nitroamino, maleimido, isothiocyanato, hydroxy, hydroxyalkyl, alkyl, alkoxy, carbamoyl, carboxamide, acylamino or carboxy moieties.

The term “aralkyl” refers to an aryl group bonded through an alkyl group.

The term “halo” refers to bromo, chloro, fluoro or iodo.

The term “alkoxy” refers to a chain consisting of C and O atoms of a 2:1 ratio in the range of 4 to 10 atoms, wherein methoxy is the most preferred alkoxy group.

The term “carboxy” refers to the group —C(O)OH or the group —C(O)OR wherein R is alkyl.

The compounds or pharmaceutically acceptable salts thereof incorporated in a suitable pharmaceutically acceptable vehicle, such as human serum albumin, and administered to a mammal intravenously, provide sufficient iodine concentration in the liver and other organs for x-ray CT imaging at dose levels of 5 mmol/kg of body weight or higher.

There is further provided a method for x-ray CT diagnostic imaging of the liver and/or other organs which comprises intravenously administering to the patient an effective contrast producing amount of the x-ray contrast composition comprising a compound of formula I, II or III.

In another aspect the present invention provides an x-ray contrast composition for diagnostic imagining of the GI tract by x-rays or CT scans wherein the composition comprises in a pharmaceutically acceptable aqueous carrier the compounds of the formula I, II or III, or a pharmaceutically acceptable salt thereof.

There is further provided a method for x-ray diagnostic imaging of the GI tract which comprises orally or rectally administering to the patient an effective contrast producing amount of the x-ray contrast composition.

DETAILED DESCRIPTION OF THE INVENTION

Some starting materials/reagents used in the synthesis of the compounds of the present invention are readily available, while others can be made by methods known in the art.

The compounds of the present invention were synthesized as shown in the following schemes.

The compound of formula I, N,N-Dimethyldiatrizoic acid (I') (hereinafter sometimes referred to as MDTA) was synthesized, as in reference H. Holtermann et al., U.S. Pat. No. 3,178,673, Apr. 13, 1965, by the N-methylation of diatrizoic acid (IV) using either methyl iodide or dimethyl sulfate in aqueous media at alkaline pH to obtain pure MDTA (>99.9% purity) as a white crystalline solid (m.p. 185° C.). Water solubility of the sodium salt was ~0.35 M. The solubility of the N-methyl-glucamine (NMG) salt was ~1.3 M.

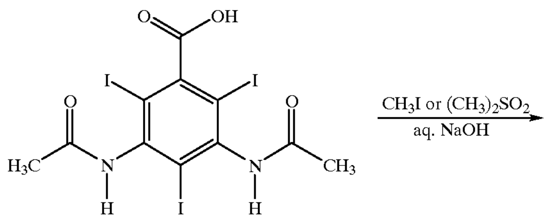

Diatrizoic acid
(IV)

-continued

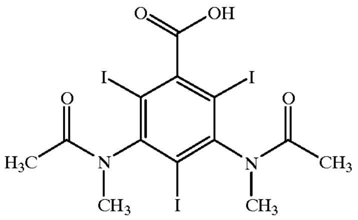

N,N-Dimethyldiatrizoic acid
(MDTA)
(I')

Compounds of formula II (A), (hereinafter sometimes referred to as fatty acid conjugates or analogs of P-MDTA or FA-PMDTA).

II

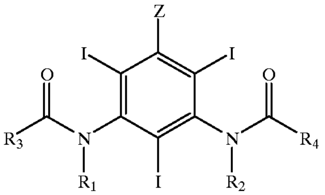

wherein

-continued

Z is

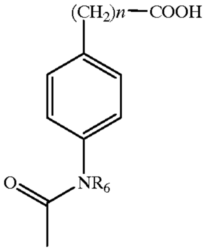

or

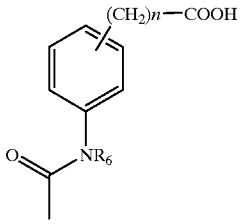

; and $R_1$, $R_2$, $R_3$, $R_4$, $R_6$ and n are as defined above, and the compounds were made as shown in Scheme 1.

MDTA-chloride (X) was made by treating MDTA (I') with thionyl chloride under reflux for 24 h.

The compounds of formula II were prepared by reaction of (4-aminophenyl) alkanoic esters (IX) with MDTA-chloride (X) in dimethylacetamide (hereinafter sometimes referred to as DMA).

In Scheme 1 specific values are denoted for n and x relating to the compounds of the illustrative working examples; however, it is to be understood that the values of n and x include the range of 0 to 24 and the alkanoic esters are attached to the ortho, meta or para positions of the amino phenyl moiety. In Scheme 1 and in working examples the abbreviation "h" denotes hour or hours, and "RT" denotes room temperature.

Scheme 1
Synthesis of fatty acid analogs of diatrizoates (FA-PMDTA)

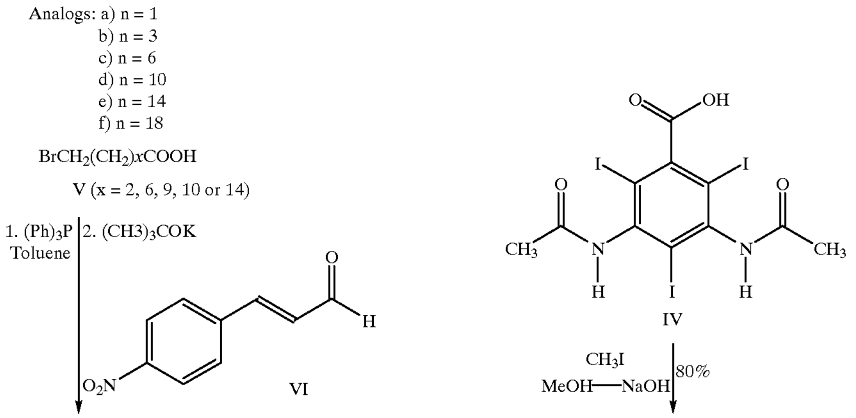

-continued

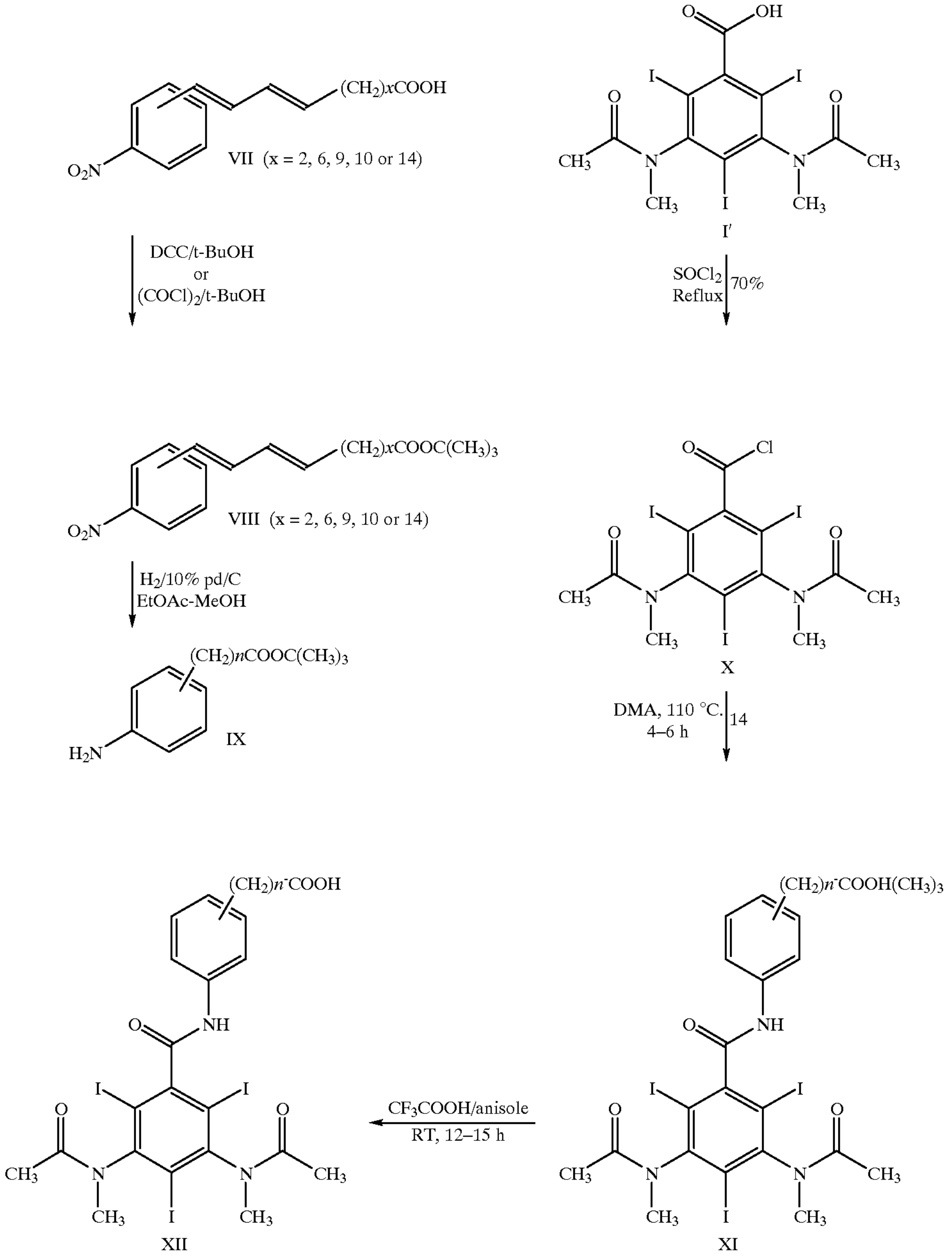

Referring to Scheme 1, ω-Bromoalkanoic acids V were converted to the corresponding phosphonium salts which when subjected to Wittig reaction with p-nitrocinnamaldehyde VI in presence of potassium t-butoxide gave the Wittig products VII. No attempts were made to separate the diene mixture. The carboxylic acid group in VII was protected as its t-butyl ester by treating with dicyclohexylcarbodiimide/tBuOH or Oxalyl chloride/t-BuOH. Catalytic hydrogenation of the diene ester VIII with 10% pd/C furnished the desired synthons, 4-aminophenylalkanoic ester IX. t-Butyl 4-(4-aminophenyl)-butyrate IX b was made in 64% yield from 4-(p-nitrophenyl)-butyric acid by esterification followed by catalytic hydrogenation. Treatment of the fatty acid synthons IX with X in DMA at 80–100° C. followed by deprotection of the resulting coupled product XI with trifluoroacetic acid (hereinafter referred to as TFA) containing anisole furnished the PMDTA fatty acid analogs of formula XII.

Compounds of formula II (B (hereinafter sometimes referred to as DP-MDTA analogs) wherein Z is 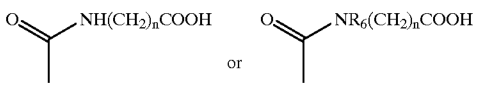 ;

and $R_6$ and n are as defined above are prepared as shown in Scheme 2 by reacting the MDTA-chloride X with ω-aminoalkanoic acids or their 1,1-dimethylethyl esters in DMA to obtain the amides of formula XIII or formula XIII'.

Scheme II
Synthesis of DP-MDTA analogs
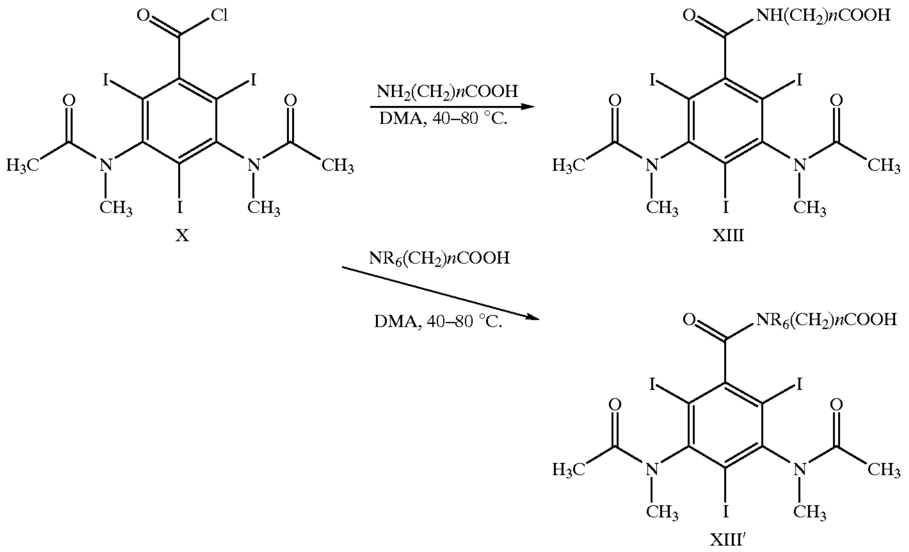
X
XIII
XIII'
wherein n and $R_6$ are as defined above.
The compounds of formula III
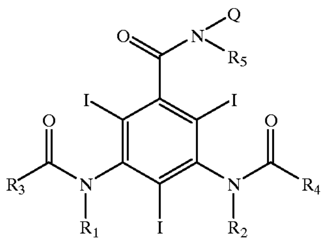
III
wherein
-continued
Q is
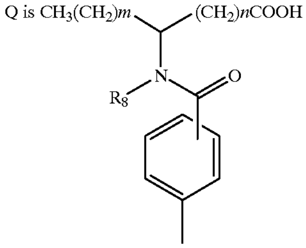
wherein
n, m, $R_1$, $R_2$, $R_3$, $R_4$, $R_5$ and $R_8$ are as defined above, were prepared as shown in Scheme 3.
Scheme 3
Synthesis of PMDTA analogs linked in the middle of the alkanoic acid chain
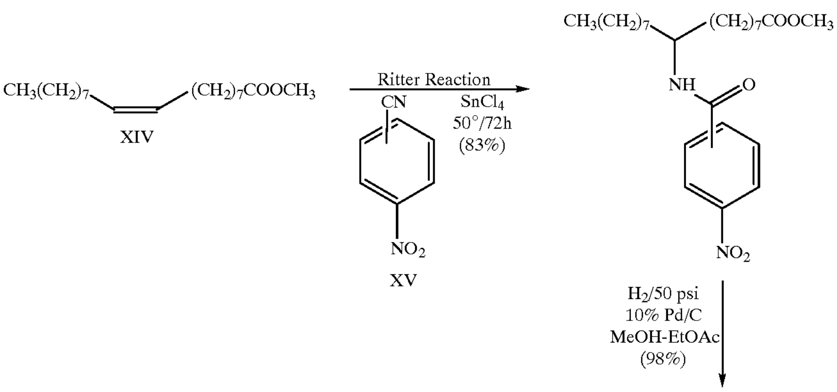
XIV
XV
XVI -continued

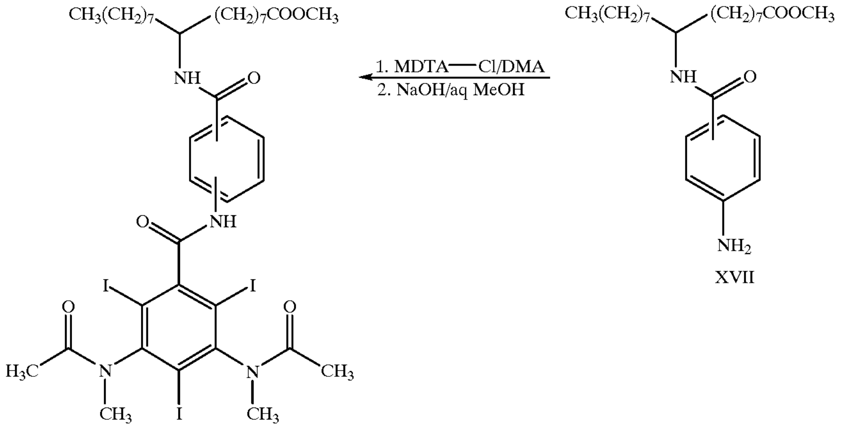

XVIII XVII

As an example, methyl oleate XIV was subjected to the Ritter reaction with p-nitrobenzonitrile XIV in the presence of $SnCl_4$ at 50° C. to obtain the phenylamido adduct XVI. Catalytic hydrogenation of XVI (10% Pd/C in MeOH—EtOAc) provided the key aniline XVII. Treatment of XVII with MDTA-chloride X followed by basic hydrolysis furnished a desired compound of formula XVIII. Similarly, starting from appropriate unsaturated fatty acids of various chain lengths, other compounds of formula XVIII could be prepared.

The compounds of formula III wherein

Q is

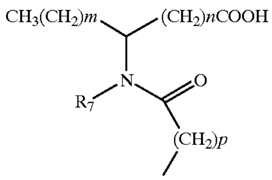

wherein m, n, p and $R_7$ are as defined above, were prepared as shown in Scheme 4.

Scheme 4

Synthesis of DPMDTA analogs linked in the middle of the alkanoic acid chain

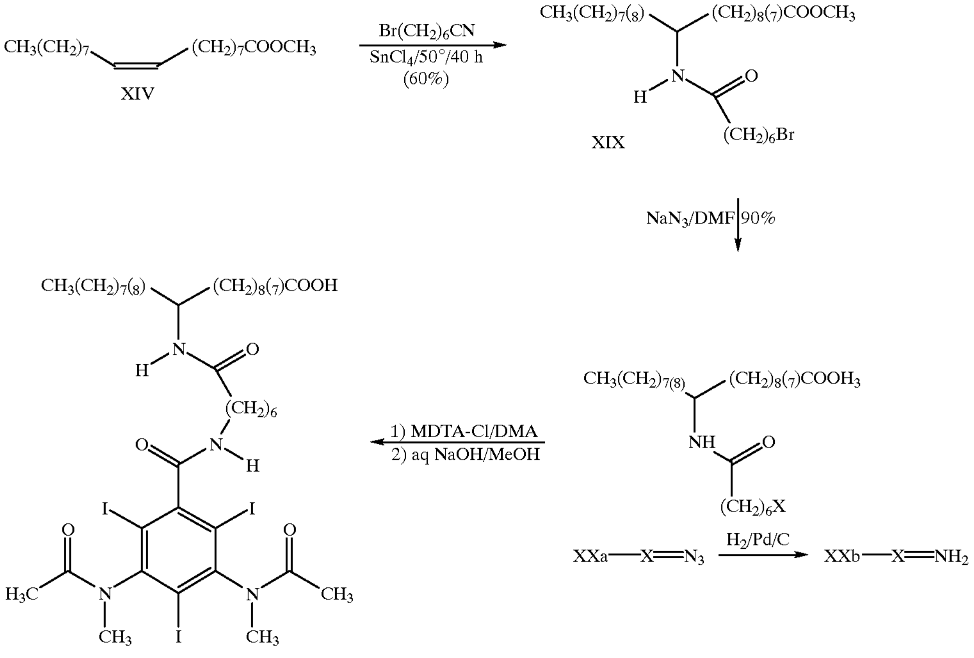

XIV XIX XXI

As an example, methyl oleate XIV was reacted with 7-bromoheptanenitrilc in the presence of $SnCl_4$ and water at 50° C. for 40 h to obtain the amide XIX. Further treatment of XIX with $NaN_3$ in DMF gave the corresponding azide XXa, which upon catalytic hydrogenation provided the amine XXb. Coupling of XXb with MDTA-chloride X in DMA followed by basic hydrolysis furnished the desired compound of formula XXI.

The following working examples will further illustrate the compounds of the present invention. The highlighted numerals in the Examples refer to compounds and moieties used in the Schemes.

Example 1

3,5-Bis-(Acetylmethylamino)-2,4,6-triiodobenzoic acid (I') (Scheme 1) MDTA)

METHOD A

To a solution of 3,5-bis-(acetylamino)-2,4,6-triiodobenzoic acid (diatrizoic acid)(IV)(6.14 g, 10 mmol) in 6.5 N aq. NaOH (10 ml) and methanol (10 ml), was added methyl iodide (7.1 g, 50 mmol) over a 5 min period, and the mixture was stirred at RT overnight (18 h). The mixture was acidified to pH 5 with con. HCl, then diluted with cold water (100 mL). The N-bis-methylated diatrizoic acid I', thus precipitated as an amorphous white solid, was collected by filtration, washed with cold water and dried; yield 5.06 g (79%).

Elemental analysis: Calc'd for $C_{13}H_{13}I_3N_2O_4$, 0.15 $H_2O$: C 24.22; H, 2.08; N, 4.35; I, 59.06; O, 9.97; Found: C, 23.80; H, 2.22; N, 4.11; I, 58.86; $H_2O$, 0.41 (KF)

Method B

A solution of dimethylsulfate in acetone (200 mL) was slowly added in drops to a stirred solution of diatrizoic acid IV (100 g, 163 mmol) in 5N KOH (200 mL) and water (100 mL) at 0–15° C. Following the addition, the mixture was stirred at RT for 44 h. Acetone was removed and the mixture acidified with concentrated HCl. The precipitated white solid was collected by filtration, washed with water, $CH_2Cl_2$, EtOAc and water. This solid upon crystallization from ETOAc/EtOH furnished pure MDTA I' as a white solid (45 g, 43%), which was identical with the product prepared by method A.

Example 2

3,5-Bis-(Acetylmethylamino)-2,4,6-triiodobenzene carbonyl chloride (X) (Scheme 1) (MDTA-Cl)

A mixture of 3,5-bis-(acetylmethylamino)-2,4,6-triiodobenzoic acid I' (1.28 g, 2 mmol) and thionyl chloride (20 mL) was stirred under reflux (bath temperature 100° C.) under nitrogen for 20 h. The excess thionyl chloride was removed under vacuum, and the residue triturated with ethyl acetate (20 mL) for 15 min. The desired acid chloride X, formed as a white amorphous solid, was collected by filtration and dried. Yield 0.95 g (70%).

Elemental analysis: Calc'd for $C_{13}H_{12}N_2O_3ClI_3$ 1.02 $H_2O$: C,23.00; H, 2.08; N, 4.13; O: 9.48, Cl:5.22, I:57.67. Found: C, 23.06; H, 1.78; N, 4.07; O: NA, Cl:5.26, I:56.45.

Example 3

4-(((3,5-Bis(Acetylmethylamino)-2,4,6-triiodophenyl)carbonyl)amino)-benzeneacetic acid (XIIa) (Scheme 1)

A mixture of MDTA-Cl X (2.18 g, 3.3 mmole) and p-aminophenylacetic acid (1.2 g, 8.27 mmole) in DMA (8 mL) was stirred at 60° C. for 30 h. The solvent was removed and the residue was treated with hot EtOAc (600 mL) containing EtOH (25 mL). The solution was filtered and the filtrate was freed of the solvent. The solid was recrystallized from EtOAc-EtOH to afford the title compound as a white amorphous solid (1.54 g, 57%).

Elemental analysis: Calc'd for $C_{21}H_{20}N_3I_3$. 0.66 $H_2O$: C 32.05; H, 2.73; N, 5.34; I, 48.38; O, 11.50. Found: C,32.34; H, 2.42; N, 5.05; I, 48.48%.

Example 4

4-(((3,5-Bis(acetylmethylamino)-2,4,6-triiodophenyl)carbonyl)amino)benzenebutyric acid (XIIb) (Scheme 1)

a. 4-Aminobenzenebutyric acid 2,2-dimethylethyl ester (IXb)

4-(p-Nitrophenyl)butyric acid (4.18 g, 20 mmol) was treated with oxalyl chloride at RT for 24 h to obtain the corresponding acid chloride, which was reacted with t-butanol (18.5 g, 250 mmol) in the presence of triethylamine (4 g, 40 mmol) at 0–5° C. to get the desired t-butyl ester (3.5 g, 66%). Hydrogenolysis of the nitro-ester (3 g) over 10%Pd/C in ethanol yielded the amino-cster IXb (3.0 g).

b. 4-(((3 5-Bis(acetylmethylamino)-2,4,6-triiodophenyl)carbonyl)amino)benzenebutyric acid 2,2-dimethylethyl ester) (XIb)

To a solution of 4-aminobenzenebutyric acid 2,2-dimethylethyl ester IXb (2.0 g, 7.5 mmol) in dimethylacetamide (DMA 25 mL), was added 3,5 bis (acetylmethylamino)-2,4,6 triiodobenzoyl chloride X (1.98 g, 3 mmol), and the mixture stirred at 90–95° C. for 6 h. The solvent was removed in vacuo and the residue was dissolved in ethyl acetate (200 mL). The organic extract was washed with saturated sodium bicarbonate (250 mL), water and saturated sodium chloride and dried over sodium sulfate. The solvent was removed in vacuum and the residue purified by a silica gel column (150 g) using hexane/EtOAc to obtain the title compound XIb (1.98 g, yield 74%). (MS: m/e 858 $(M-H)^-$.

c. 4-(((3.5-Bis(acetylmethylamino)-2,4.6-triiodophenyl)carbonyl)amino)benzenebutyric acid (XIIb)

To the t-butylester XIb (1.98 g) were added anisole (6 mL) and TFA (20 mL) and the solution was stirred at room temperature for overnight. The solution was evaporated to dryness and trace amounts of anisole and TFA were removed by repeated evaporating with water to give a solid (1.78 g, 99%). The solid was recrystallized from EtOH—EtOAc to obtain the pure XIIb. (MS: m/e 804 $[M+H]^+$ Elemental analysis: Calc'd for C H $N_3I_3O_5$: C 34.18; H, 3.06; N, 5.20; I, 47.11. Found: C,34.38; H, 2.84; N, 5.0; I, 46.69.

Example 5

4-[[[3,5-Bis(acetylamino)-2,4,6-triiodophenyl]carbonyl]amino]-benzeneheptanoic acid (XIIc) (Scheme 1)

a. 4-Aminobenzenehcptanoic acid 1,1-dimethylethyl ester (IXc)

To a solution of 7-(4-nitrophenyl)4,6-heptadicnic acid, 1,1-dimethyl ester (0.6 g, 1.98 mmol, 1.0 equiv.) in methanol (50 mL) and ethyl acetate (5 mL) was added 10% Pd/C (0.5 g). The mixture was hydrogenated at 50 psi for 55 h. The catalyst was filtered off. The filtrate was concentrated to dryness and the residue was purified by chromatography over a silica gel column to afford pure IXc (0.46 g, 84%). MS: m/e 278 $(M+H)^+$ b. 4-[[[3,5-Bis(acetylmethylamino)-2,4,6-triiodophenyl]carbonyl]amino]benzeneheptanoic acid 1,1-dimethylethyl ester (XIc)

To a solution of 4-aminobenzeneheptanoic acid 2,2-dimethylethyl ester IXc (185 mg, 0.67 mmol) in dimethylacetamide (DMA, 5 mL), was added 3,5-bis (acetylmethylamino)-2,4,6-triiodobenzoyl chloride X (220 mg, 0.33 mmol), and the mixture was stirred at 90–95° C. for 6 h. The solvent was removed in vacuo, and the residue was taken up in ethyl acetate (60 mL). The ethyl acetate solution was washed with cold aq. $NaHCO_3$ followed by water and saturated NaCl solution, and dried over sodium sulfate. Removal of the solvent gave a brown solid (0.6 g) which was purified by column chromatography over silica gel (40 g) using hexane/EtOAc to obtain the carboxamide XIc as an amorphous solid; yield 148 mg (50%).

c. 4-[[[3,5-Bis(acetylmethylamino)-2,4,6-triiodophenyl]carbonyl]amino]benzeneheptanoic acid (XIIc)

To a solution of the t-butyl ester XIc obtained in Example 5b (125 mg, 0.14 mmol) in anisole (1 mL) was added trifluoroacetic acid (4 mL) and the solution was stirred at RT for 12 h. The solvents were removed in vacuo, and the residue was triturated with hexane (10 mL). The hexanes were removed to give a semi solid (125 mg) which was crystallized from ethyl acetate (3–4 mL) to furnish the title compound XIIc as a white amorphous solid (60 mg, yield 52%).

Elemental analysis: Calc'd for $C_{26}H_{30}I_3N_3O_5$ (845.22): C, 36.95; H, 3.58; N, 4.97; I, 45.04; O, 9.46. Found: C, 36.99; H, 3.31; N, 4.62; I, 44.86%.

Example 6

4-[[[3,5-Bis(acetylmethylamino)-2,4,6-triiodophenyl]amino]-benzeneundecanoic acid (XIId)

a. 4-Aminobenzeneundecanoic acid 1,1-dimethylethyl ester (IXd)

To a solution of 11-(4-nitrophenyl)8-10-undecadienoic acid 1,1-dimethyl ester (2.0 g, 5.57 mmol, 1.0 equiv.) in methanol (100 ml) and ethyl acetate (15 ml) was added 10% Pd/c (0.5 g). The mixture was hydrogenated at 50 psi for 24 h. The catalyst was filtered off. The filtrate was concentrated to dryness to give 1.7 g 95.4% yield) of the crude product which upon purification by a silica gel column ($CH_2Cl_2$:hexane 1.5:1) gave 1.35 g (73% yield) of pure compound.

Microanalysis: Cal'd for $C_{21}H_{35}NO_2$: C:75.63, H:10.58, N:4.20, O:9.59. Found: C: 75.56, H: 10.68, N: 4.63, O:NA.

b. 4[[[3,5-Bis(acetylmethylamino)-2,4,6-triiodophenyl]carbonyl]amino]benzeneundecanoic acid 1,1-dimethylethyl ester (XId)

To a solution of 4-aminobenzeneundecanoic acid 2,2-dimethylethyl ester IXd (0.5 g, 1.5 mmol) in dimethyl acetamide (DMA, 5 mL), was added 3,5-bis (acetylmethylamino)-2,4,6-triiodobenzoyl chloride X (0.34 g, 0.55 mmol), and the mixture was stirred at 100° C. for 5 h. The solvent was removed in vacuo, and the residue was taken up in ethyl acetate (60 mL). The ethyl acetate solution was washed with cold aq. $NaHCO_3$ followed by water and saturated NaCl solution, and dried over sodium sulfate. Removal of the solvent gave a brown solid (0.76 g) which was purified by column chromatography over silica gel (40 g) using hexane-ethyl acetate to obtain the carboxamide XId as an amorphous solid; yield 0.28 g (58%).

Elemental analysis: Calc'd for $C_{34}H_{46}N_3I_3O_5$ (957.5): C, 42.65; H, 4.84; N, 4.39; I, 39.76; O, 8.36; Found: C, 42.78; H, 4.92; N, 4.52; I, 39.61%.

c. 4-[[[3,5-Bis(acetylmethylamino)-2,4,6-triiodophenyl]carbonyl]amino]benzeneundecanoic acid (XIId)

To a solution of the t-butyl ester XId of Example 6b (180 mg, 0.188 mmol) in anisole (1 mL) was added trifluoroacetic acid (5 mL) and the solution was stirred at RT for 12 h. The solvents were removed in vacuo, and the residue was triturated with hexane (10 mL). The hexanes were removed to give a semi solid (175 mg) which was crystallized form ethyl acetate (3–4 mL) to furnish the title compound XIId as a white amorphous solid (147 mg, yield 87%).

Elemental analysis: Calc'd for $C_{30}H_{38}N_3I_3O_5$ $H_2O$(0.43): C, 39.64; H, 4.31; N, 4.62; I, 41.88; O, 9.55. Found: C, 39.75; H, 4.19; N, 4.51; I, 41.69, $H_2O$ 0.85%.

Example 7

4[[[3,5-Bis(acetylmethylamino)-2,4,6-triiodophenyl]carbonyl]amino]benzenepentadecanoic acid (XIIe) (Scheme 1)

a. [4-Aminobenzenepentadecanoic acid 1,1-dimethylethyl ester (IXe)

To a solution of 15-[4-nitrophenyl] 12,14-pentadecienoic acid, 1,1-dimethylethyl ester (1.40 g, 3.4 mmol) in methanol (80 ml) and ethyl acetate (20 ml) was added 10% Pd/C (0.3 g). The mixture was hydrogenated at 50 psi for 20 h. The catalyst was filtered off. The filtrate was concentrated to dryness and to give 1.28 g (97.5% yield) of the crude product, which was purified by a silica gel column to obtain IXe (1.08 g (82.3% yield). MS: m/e 390 $(M+H)^+$.

b. 4 -[[[3,5-Bis(acetylmcthylamino)-2,4,6-triiodophenyl]carbonyl]amino]benzenepentadecanoic acid 1,1-dimethylethyl ester (XIe)

To a solution of 4-aminobenzenepentadecanoic acid 2,2-dimethyl ester IXe of Example 7a (430 mg, 1.1 mmol) in dimethylacetamide (DMA, 10 mL), was added 3,5-bis (acetylmethylamino)-2,4,6-triiodobenzoyl chloride X (365 mg, 0.55 mmol), and the mixture was stirred at 100° C. for about 5 h. The solvent was removed in vacuo, and the residue was taken up in ethyl acetate (60 mL). The ethyl acetate solution was washed with cold aq. $NaHCO_3$ followed by water and saturated NaCl solution, and dried over sodium sulfate. Removal of the solvent gave a brown solid (0.78 g) which was purified by column chromatography over silica gel (60 g) using hexane-ethyl acetate to obtain the carboxamide XIe as an amorphous solid; yield 360 mg (65%).

Elemental analysis: Calc'd for $C_{38}H_{54}N_3I_3O_5$ (1013.53): C, 45.03; H, 5.37; N, 4.15; I, 37.56; O, 7.89; Found: C, 44.62, H, 5.23; N, 4.15; I, 37.54%.

c. 4-[[[3,5-Bis(acetylmethylamino)-2,4,6-triiodophenyl]carbonyl]amino] benzenepentadecanoic acid (XIIe)

To a solution of 4-[[[3,5-bis(acetylmethylamino)-2,4,6-triiodophenyl]carbonyl]amino]-benzenepentadecanoic acid, 1.1-dimethylethyl ester XIe of Example 7b (30 mg, 0.3 mmol) in anisole (1 mL), was added trifluoroacetic acid (10 mL) and the mixture stirred at RT overnight (15 h). The solvents were removed in vacuo, and the residue crystallized from ethyl acetate to furnish pure XIIe as a white amorphous solid (205 mg, yield 70%, purity>98%). Additional product (35 mg, purity 96%) was obtained from the mother liquor for a total yield of 81%.

Elemental analysis: Calc'd for $C_{34}H_{46}N_3I_3O_5$ (957.5): C, 42.65; H, 4.84; N, 4.39; I, 39.76; O,8.36; Found: C, 42.67; H, 4.89; N, 4.42; I, 39.55%.

Example 8

4-[[[3,5-Bis(acetylmethylamino)-2,4,6-triiodophenyl]carbonyl]amino] benzenepentadecanoic acid (XIIf) (Scheme 1)

a. 19-[4-Aminobenzene nonadecanoic acid 1,1-dimethylethyl ester (IXf)

To a solution of 19-[4-nitrophenyl] 16,18-nonadecadienoic acid, 1,1-dimethylethyl ester (1.45 g, 3.09 mmol, 1.0 equiv.) in methanol (30 ml) and ethyl acetate (30 ml) was added 10% Pd/C (0.46 g). The mixture was hydrogenated at 50 psi for 20 h. The catalyst was filtered off. The filtrate was concentrated to dryness to give 1.32 g (94% yield) of the crude product, which was purified by a silica gel column to give 0.85 g (62% yield) of the pure product IXf.

Elemental Analysis: $C_{29}H_{51}NO_2$, C: 78.15, H: 11.53, N: 3.14, O: 7.18. Found: C: 78.18, H: 11.46, N: 3.07.

b. 4-[[[3,5-Bis(acetylmethylamino)-2,4,6-triiodophenyl]carbonyl]amino] benzenepentadecanoic acid 1,1-dimethylethyl ester (XIf)

To a solution of 4-aminobenzene-nonadecanoic acid 2,2-dimethylethyl ester IXf (356 mg, 0.8 mmol) in dimethylacetamide (DMA, 3 mL), was added 3,5-bis-(acetylmethylamino)-2,4,6-triiodobenzoyl chloride X (264 mg, 0.4 mmol), and the mixture was stirred at 100° C. for about 6 h. The solvent was removed in vacuo, and the residue was taken up in ethyl acetate (60 mL). The ethyl acetate solution was washed with cold aq. $NaHCO_3$ followed by water and saturated NaCl solution, and dried over sodium sulfate. Removal of the solvent gave a brown solid (605 mg) which was purified by column chromatography over silica gel to obtain the carboxamide title compound XIf as an amorphous solid (258 mg, yield 60%).

Elemental analysis: Calc'd for $C_{42}H_{62}N_3I_3O_5$ (1069.64): C, 47.16; H, 5.84; N, 5.84; I, 35.59; O, 7.48; Found: C, 47.10, H, 5.88; N, 3.76; I, 34.42%.

c. 4-[8 [3,5-Bis(acetylmethylamino)-2,4,6-triiodophenyl]carbonyl]amino]-benzenenonadecanoic acid (XIIf)

To a solution of the t-butyl ester XIf (182 mg, 0.17 mmol) in anisole (1 mL) was added trifluoroacetic acid (5 mL) and the solution was stirred at RT for 12 h. The solvents were removed in vacuo, and the residue was triturated with hexane (10 mL). The hexanes were removed to give a semi solid (170 mg) which was crystallized from ethyl acetate (3–4 mL) to furnish the title compound XIIf as a white amorphous solid (126 mg, yield 73%).

Elemental analysis: Calc'd for $C_{38}H_{54}N_3I_3O_5$: C, 45.03; H, 5.37; N, 4.15; I, 37.56; O, 7.89; Found: C, 44.86; H, 5.41; N, 4.22; I, 39.93%.

Example 9

4-[[[3,5-Bis(acetylmethylamino)-2,4,6-triiodophenyl]carbonyl]amino]-acetic acid (XIIIa)

To a mixture of aminoacetic acid 1,1-dimethylethyl ester (glycine t-butyl ester) HCl salt (1.1 g, 6.6 mmol) in DMA (20 mL) and triethylamine (1.38 mL, 9.9 mmol, 4.5), was added MDTA-Cl X (1.45 g), 2.2 mmol). The mixture was stirred at 80° C. for 4 h. DMA was removed in vacuo and the crude product was purified by a silica gel chromatography (EtOAc/hexane 3:7) to give pure carboxamide 1.22 g (74%). This product was treated with TFA (24 mL) and anisole (2.3 mL) for 6 h at RT. The solvents were removed. The product was washed with hexane and water. The crude was recrystallized from EtOAc/hexane to furnish the pure title compound XIIIa (0.94 g, 83%).

Elemental analysis: Calc'd for $C_{15}H_{16}N_3O_5I_3$: 0.2 EtOAc: C, 26.48; H, 2.48; N, 5.86; O, 12.06; I,53.12; Found: C, 26.55; H, 2.40; N,6.06; I, 52.88%.

Example 10

4-[[[3,5-Bis(acetylmethylamino)-2,4,6-triiodophenyl]carbonyl]amino]-butanoic acid (XIIIb)

To a mixture of MDTA-Cl (X) (2.0 g, 3 mmol) in DMA (10 mL) was added 4-aminobutanoe acid (0.93 g, 9 mmol) at 0–15° C. The mixture was stirred at RT for 40 h. DMA was removed in vacuo and water was added. Then the crude product that separated out was collected and recrystallized from EtOAc/EtOH) to give the title compound XIIIb (0.54 g, 25%). The aqueous solution, upon chromatography over a CHP-20 column furnished additional product (0.43 g (total yield 0.97 g, 45%).

Elemental analysis: Calc'd for $C_{17}H_{20}N_3O_5I_3$: 0.35 $H_2O$: C, 37.84; H, 2.84; N, 5.73; O, 11.66; I, 51.92; Found: C, 28.19; H, 2.85; N, 5.47; I, 52.01%.

Example 11

4[[[3,5-Bis(acetylmethylamino)-2,4,6-triiodophenyl] carbonyl]amino]-heptanoic acid (XIIIc)

To a solution of 7-aminoheptanoic acid (0.8 g, 5.5 mmol) in DMA (20 mL) was added MDTA-Cl (X) (2.8 g, 4.2 mmol) and the mixture stirred at 80° C. for 24 h. DMA was removed. To the residue water was added. The solid material was collected and recrystallized from EtOH to furnish the pure title compound XIIIc (1.02 g, 31%).

Elemental analysis: Calc'd for $C_{20}H_{26}N_3O_5I_3$: 0.18 EtOAc: C, 31.70; H, 3.52; N, 5.35; O, 10.92; I, 48.50; Found: C, 31.70; H, 3.13; N, 5.28; I, 48.49%.

Example 12

4-[[[3,5-Bis(acetylmethylamino)-2,4,6-triiodophenyl]carbonyl]amino]-dodecanoic acid (XIIId)

To a solution of 12-aminododecanoic acid (1.1 g, 4.9 mmol) in DMA (25 mL) was added MDTA-Cl (X) (2.5 g, 3.8 mmol) and the mixture stirred at 80–85° C. for 39 h. DMA was removed and the product was purified by a CHP-20 column to furnish the pure title compound XIIId (1.6 g, 50%).

Elemental analysis: Calc'd for $C_{25}H_{36}N_3O_5I_3$: 0.33 $H_2O$: C, 36.31; H, 4.57; N, 4.77; O, 11.16; I, 43.20; Found: C, 36.71; H, 4.29; N, 4.86; I, 43.58%.

Example 13

9(10)-N-(4-(((3,5-bis(acetylmethylamino)-2,4,6-triiodophenyl]carbonyl]amino]benzoyl)amino-octadecanoic acid (XVIII)

a. Methyl 9/10[p-nitrobenzoylamino]octadecanoate (XVI)

To a mixture of methyl oleate XIV (592 mg, 2 mmol) and p-nitrobenzonitrile XV (296 mg, 2 mmol), was added $SnCl_4$ (572 mg, 2.4 mmol) followed by water (43 mg, 2.4 mmol). The mixture was stirred at 50–60° C. for 70 h. This was taken up in ether (200 mL) and washed with water followed by aq. $NaHCO_3$ solution. The organic extract was dried and concentrated to yield a brownish solid (0.9 g). The material was purified by flash chromatography over a column of silica gel eluting with gradient hexane/ethyl acetate to obtain methyl 9/10[p-nitrobenzamido]octadecanoate XVI as a white solid (620 mg, 67%). MS: m/e 463 $(M+H)^+$.

b. Methyl 9/10[p-aminobenzoylamino] octadecanoate (XVII)

Methyl 9/10[p-nitrobenzamido]octadecanoate XVI of Example 13a (5.08 g, 11 mmol) was dissolved in a mixture of EtOAc/EtOH (2:1) (100 mL) and the solution was purged with nitrogen. After the addition of 10% Pd/C (0.5 g), the mixture was hydrogenated at 50 psi for 24 h. The catalyst was filtered off, and the filtrate was concentrated to furnish the corresponding amine XVII as a highly viscous oil (4.74 g, 99%). MS: m/e 433 $(M+H)^+$.

c. 9(10)-N-(4-(((3,5-Bis-(acetylmethylamino)-2,4,6-triiodophenyl)carbonyl)amino)benzoyl)amino-octadecanoic acid (XVIII)

A mixture of MDTA-Cl X and 9(10)-octadecanoate analog XVII of Example 13b in DMA was stirred at 60° C. for 30 h, and then at 80° C. for 15 h. The solvent was removed and the product was purified by column chromatography. This product was then treated with 10% aq. methanolic KOH overnight. The mixture was acidified and the solid was collected. Recrystallization from ethanol furnished the pure compound XVIII as a white solid (0.53 g; 76% yield). MS: m/e 1043 $(M+H)^+$.

Elemental analysis: Calc'd for $C_{38}H_{53}N_4O_6I_3$ C: 43.78; H: 5.12; N: 5.37; O: 9.21, I: 36.52. Found: C: 43.98, H: 5.25, N: 5.17, I: 36.86.

Example 14

9(10)-N-(7-(((3,5-Bis-(acetylmethylamino)-2,4,6-triiodophenyl)carbonyl)amino)heptanoyl)amino-octadecanoic acid (XXI)

a. Methyl 9(10)-(7-bromoheptanoylamino)-octadecanoate (XIX)

Methyl oleate XIV (2.9 g, 10 mmol) was treated with 7-bromoheptanenitrile (1.9 g, 10 mmol) and water (0.2 mL, 11 mmol). The mixture was stirred at room temperature for 10 min and then at 50° C. for 40 h. The mixture was dissolved in EtOAc and washed with aqueous $NaHCO_3$ and water. The organic extract was concentrated and the residue was purified by silica gel chromatography to obtain pure XIX (3.02 g, 60%). MS: m/e 506, 504 $(M+H)^+$.

b. Methyl 9(10)-(7-Azidoheptanoylamino)-octadecanoate (XXa)

A mixture of bromoheptanoyl derivative XIX (2.92 g, 5.8 mmol) and $NaN_3$ (0.74 g, 11.6 mmol) in DMF (15 mL) was stirred at 50° C. for 40 h. The solvent was removed in vacuo and the residue was redissolved in EtOAc. The organic extract was washed with water, dried, and concentrated. The residue was purified by silica gel chromatography to afford pure azide XXa (2.2 g, 81.4%). MS: m/c 467 $(M+H)^+$.

c. Methyl 9(10)-(7-aminoheptanoylamino)-octadecanoate (XXb)

A solution of the above azide XXa (21 g, 4.5 mmol) in MeOH was stirred with Lindlar catalyst (5% $Pd/CaCO_3$) (1.04 g) under 1 atmosphere of hydrogen at RT for 20 h. The catalyst was filtered off and the filtrate was concentrated. The crude product was purified by silica gel chromatography to obtain the corresponding pure amine XXb (1.78 g, 90% yield). MS: m/e 440 $(M+H)^+$.

d. 9(10)-N-(7-(((3.5-Bis-(acetylmethylamino)-2,4,6-triiodophenyl)carbonyl)amino)heptanoyl)amino-octadecanoic acid (XXI)

A mixture of MDTA-Cl (X) (1.32 g, 2 mmol) and 9(10)-methyl (7-aminoheptanoylamino)octadecanoate derivative XXb (1.8 g, 4.2 mmol) in DMA was stirred at 80° C. for 24 h. The solvent was removed and the product was purified by silica gel column chromatography to obtain the ester intermediate (0.8 g, (38%). This product was then treated with 10% aq. methanolic KOH overnight. The mixture was acidified and the obtained solid was collected. Recrystallization from ethanol furnished the title compound XXI (0.53 g, 76%).

Elemental analysis: Calc'd for $C_{38}H_{53}N_4O_6I_3$: (1042): C, 43.78; H, 5.12; N, 5.37; I, 36.52; O, 9.21; Found: C, 43.98; H, 5.25; N,5.17; I, 35.86%.

RADIO LABELING

Radioiodination

All of the new analogs were radiolabeled in order to determine their physical and biological properties. The iodinated compounds were exchange-labeled by heating with $Na^{125}I$ in the presence of $CuSO_4$ and $Na_2S_2O_5$ in glacial acetic acid at 135–150° C. for 1 h, followed by HPLC purification using a nucleosil C18 column and $CH_3CN$—$H_2O$ containing 0.1% TFA as an eluent. In some cases (e.g. the compound of Example 12) the radioiodination was carried out by heating with Na*I in HOAc—NaOAc (pH 4.6) at 100° C. for 15 min. In all cases radiolabeled compounds of acceptable radiochemical purity and specific activity were obtained.

The compound of formula I, N,N-dimethyl-diatrizoic acid, was similarly radiolabeled for biological studies.

Vehicles Used For Incorporating the Compounds of the Present Invention a) For intravenous administration the preferred vehicle for the compounds of formula I, II and III is bovine serum albumin, however, other physiologically acceptable vehicles may also be used.

b) For oral and rectal administration the compounds of formula I, II and III are incorporated in physiologically acceptable carriers or excipients in a manner within the skill of the art.

The compounds with the addition of pharmaceutically acceptable aids (such as surfactants and emulsifiers) and excipients may be suspended or partially dissolved in an aqueous medium resulting in a dispersion, solution or suspension. However, the oily contrast agents arc preferably made into emulsions.

Compositions of the present invention typically comprise the following pharmaceutically acceptable components based on % w/v:

Non aqueous phase 1–50

Contrast Agent 0.001–75

Excipient 0–20

Aids/Surfactants/Emulsifiers 0.01–15 water q.s. to 100

The nonaqueous phase comprises vegetable oils such as safflower oil; non-metabolizing fat substituents, such as Simplesse; fluorinated hydrocarbons, such as perfluorodecalin; mineral oil and simethicone.

Excipients advantageously used in the formulations include viscosity mediating and stabilizing agents, such as microcrystalline cellulose, methylcellulose, hydroxypropyl methylcellulose and gum arabic. Physiologically acceptable substances may also be included, such as sodium citrate, sodium chloride, therapeutic substances, antacid substances and flavoring agents. The inclusion of antimicrobial/antiseptic agents such as methyl parahydroxybenzoate, ethyl para-hydroxybenzoate, propyl para-hydroxybenzoate, benzoic acid or sorbic acid may also be desirable in some formulations.

As known by those skilled in the art, surfactants or emulsifiers can reduce the interfacial tension between two immiscible phases, i.e. oil-in-aqueous medium. These agents can be used alone or in combination with other emulsifying agents and surfactants. For example, Dow Corning Medical Antifoam AF, which is a composition of 30% w/v polydimethylsiloxane (simethicone) and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The amount of such surfactants may be in the range of form 0.01 to 15% w/v of the aqueous formulations, although the amount, in general, is kept as low as possible, preferably in the range of 0.05 to 5% w/v. The surface active agents may be cationic, anionic, nonionic, zwitterionic or a mixture of two or more of these agents.

Suitable cationic surfactants include cetyl, trimethyl ammonium bromide. Suitable anionic agents include sodium lauryl sulphate, sodium heptadecyl sulphate, alkyl benzenesulphonic acids and salts thereof, sodium butylnapthalene sulfonate and sulphosuccinates.

In preparing the formulations of the present invention we prefer to use nonionic emulsifiers or surface active agents. In the nonionic emulsifying agents the proportions of hydrophilic and hydrophobic groups are about evenly balanced. They differ from anionic and cationic surfactants by the absence of charge on the molecule and, for that reason, are generally less of an irritant than the cationic or anionic surfactants. Nonionic surfactants include carboxylic esters, carboxylic amides, ethoxylated alkylphenols and ethoxylated aliphatic alcohols.

The dosages of the present invention will be in the range of from about 0.1 to about 16.0 g iodine/kg body weight, preferably in the range of from about 0.5 to about 6.0 g iodine/kg body weight, and most preferably in the range of from about 1.2 to about 2.0 g iodine/kg body weight for regular x-ray visualization of the GI tract. For CT scanning, the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

The concentration of the contrast agent should be in the range of from about 0.001% w/v to about 75% w/v of the formulation, preferably from about 0.05% w/v to about 50% w/v and most preferably of from about 0.1% to about 20% w/v.

Biodistribution studies were conducted in mice and the results are given in Table I. X-Ray CT images of MDTA in mice and rats indicate that these hydrophobic diatrizoate analogs may be of promise for liver imaging.

TABLE I

Biodistribution of MDTA, P-MDTA and DP-MDTA in MICE # (% ID/g-tissue)

| # | Compound | Blood | | | Kidney | | | Liver | | | Sm/Lrg. Intestine | | | Remarks |
|---|---|---|---|---|---|---|---|---|---|---|---|---|---|---|
| | | 1' | 5' | 60' | 1' | 5' | 60' | 1' | 5' | 60' | 1' | 5' | 60' | |
| 1 | MDTA | 4.56 | 1.21 | 0.00 | 37.57 | 21.50 | 0.18 | 15.75 | 15.40 | 0.85 | 1.50 | 4.55 | 13.35 | Tracer level |
| | MDTA-Na | 6.21 | 3.03 | 0.16 | 12.97 | 12.72 | 0.96 | 13.23 | 17.56 | 2.42 | 1.81 | 3.92 | 17.02 | 0.18M |
| | MDTA-NMG | 6.63 | 3.66 | 0.12 | 13.53 | 12.65 | 0.81 | 12.30 | 16.23 | 2.13 | 2.03 | 3.80 | 16.48 | 0.19M |
| 2 | F2-P-MDTA | 4.83 | 0.96 | 0.04 | 11.48 | 5.83 | 0.33 | 17.88 | 12.87 | 2.25 | 2.47 | 9.54 | 25.42 | All tracer level |
| 3 | F4-P-MDTA | 3.55 | 0.57 | 0.07 | 5.63 | 5.41 | 0.63 | 29.65 | 29.45 | 6.13 | 1.71 | 4.56 | 20.43 | |
| 4 | F7-P-MDTA | 2.38 | 0.57 | 0.15 | 4.28 | 2.94 | 0.30 | 39.53 | 37.19 | 5.02 | 1.38 | 6.20 | 26.75 | |
| 5 | F11-P-MDTA | 9.14 | 0.74 | 0.08 | 6.21 | 3.63 | 0.10 | 57.93 | 60.13 | 2.96 | 1.14 | 3.06 | 38.21 | |
| 6 | F15-P-MDTA | 24.65 | 4.28 | 0.12 | 8.28 | 5.10 | 0.34 | 46.37 | 76.33 | 6.18 | 2.13 | 4.85 | 43.68 | |
| 7 | F19-P-MDTA | 36.72 | 13.17 | 0.68 | 5.56 | 5.45 | 2.67 | 17.24 | 24.68 | 10.41 | 1.05 | 2.40 | 14.41 | |
| 8 | F2-DP-MDTA | 4.57 | 0.81 | 0.03 | 17.07 | 5.69 | 0.16 | 12.75 | 10.60 | 1.03 | 1.28 | 8.81 | 16.47 | |
| 9 | F4-DP-MDTA | 4.91 | 0.82 | 0.12 | 17.91 | 7.89 | 0.05 | 16.11 | 11.91 | 0.33 | 1.73 | 11.33 | 21.17 | |
| 10 | F7-DP-MDTA | 2.44 | 0.57 | 0.05 | 9.50 | 8.33 | 0.16 | 17.05 | 9.81 | 0.77 | 4.92 | 14.47 | 22.19 | |
| 11 | F12-DP-MDTA | 2.38 | 0.39 | 0.04 | 9.89 | 5.72 | 0.07 | 28.89 | 16.56 | 2.17 | 2.28 | 11.62 | 28.01 | |
| 12 | 9/10-F-18P-MDTA | 6.16 | 0.46 | 0.26 | 3.32 | 2.09 | 0.39 | 30.29 | 32.33 | 3.16 | 0.51 | 2.71 | 20.21 | |

Having described the invention, it is understood that changes and modifications may be effected within spirit and scope of the invention.

What is claimed is:

1. A compound of formulae II or III or a pharmaceutically acceptable salt thereof,

II

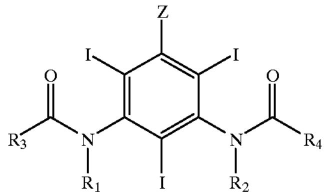

III

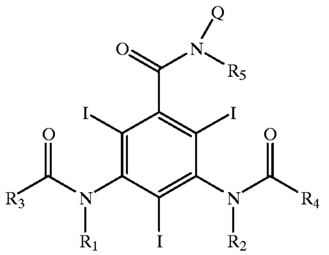

wherein

Z is 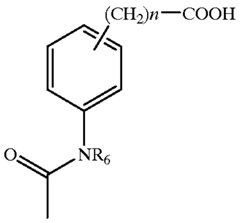 ,

Q is 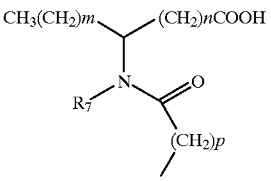 or 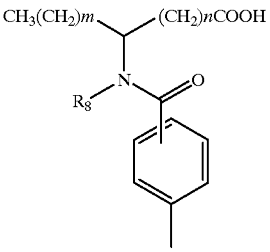 ;

$R_1$, $R_5$, $R_7$ and $R_8$ are the same or different and are hydrogen, alkyl, substituted or unsubstituted cycloalkyl, substituted or unsubstituted aralkyl, substituted or unsubstituted aryl, haloalkyl, hydroxyalkyl, alkoxyalkyl, carboxyalkyl or carboxamido alkyl;

$R_2$ and $R_3$ are hydrogen;

$R_3$ and $R_4$ are methyl;

n is 2 or 3; and m and p are the same or different and are 0–24 with the proviso that $m+n \leqq 24$.

2. A compound according to claim 1 wherein said cycloalkyl is substituted with at least one substituent selected from the group consisting of alkyl, halogen, hydroxy, hydroxyalkyl, alkoxy, alkanoyl, alkanoyloxy, amino, alkylamino, dialkylamino, alkanoylamino, thiol, alkylthiol, nitro, cyano, carboxy, carbamoyl, alkoxycarbonyl, alkylsulfonyl and sulfonamido.

3. A compound according to claim 1 wherein said aryl is phenyl, pyridyl, furanyl, thiophenyl, pyrrolyl or imidazolyl.

4. A compound according to claim 3 wherein said aryl is substituted with at least one moiety selected from the group consisting of halogen, nitroamino, maleimido, isothiocyanato, hydroxy, hydroxyalkyl, alkyl, alkoxy, carbamoyl, carboxamide, acylamino and carboxy.

5. The compound according to claim 1 selected from the group consisting of:

4-(((3,5-Bis(Acetylmethylamino)-2,4,6-triiodophenyl) carbonyl)amino)benzeneacetic acid;

4-(((3,5-Bis(acetylmethylamino)-2,4,6-triiodophenyl) carbonyl)amino)benzenebutyric acid 1,1-dimethylethyl ester;

4-(((3,5-Bis(acetylmethylamino)-2,4,6-triiodophenyl) carbonyl)amino)benzenebutyric acid;

4-[[[3,5-Bis(acetylmethylamino)-2,4,6-triodopheny] carbonyl]amino]-benzeneheptanoic acid;

4-[[[3,5-Bis(acetylmethylamino)-2,4,6-triiodophenyl] carbonyl]amino]-benzeneheptanoic acid 1,1-dimethylethyl ester;

4-[[[3,5-Bis(acetylmethylamino)-2,4,6-triiodophenyl] carbonyl]amino]-benzeneundecanoic acid;

4-[[[3,5-Bis(acetylmethylamino)-2,4,6-triiodopheny] carbony]amino]-benzeneundecanoic acid 1,1-dimethylethyl ester;

4-[[[3,5-Bis(acetylmethylamino)-2,4,6-triiodophenyl] carbonyl]amino]-benzenepenta-decanoic acid;

4-[[[3,5-Bis(acetylmethylamino)-2,4,6-triiodophenyl] carbonyl]amino]-benzenepenta-decanoic acid 1,1-dimethylethyl ester;

4-[[[3,5-Bis(acetylmethylamino)-2,4,6-triiodophenyl] carbonyl]amino]-benzene-nonadecanoic acid 1,1-dimethylethyl ester;

4-[[[3,5-Bis(acetylmethylamino)-2,4,6-triiodophenyl] carbonyl]amino]-benzene-nonadecanoic acid;

9(10)-N-(4-(((3,5-Bis-(acetylmethylamino)-2,4,6-triiodophenyl)carbonyl)amino)benzoyl)amino-octadecanoic acid;

9(10)-N-(4-(((3,5-Bis-(acetylmethylamino)-2,4,6-triiodophenyl)carbonyl)amino)-benzoyl)amino-octadecanoic acid methyl ester;

9(10)-N-(7-(((3,5-Bis-(acetylmethylamino)-2,4,6-triiodophenyl)carbonyl)amino)-heptanoyl)amino-octadecanoic acid;

9(10)-N-(7-(((3,5-Bis-(acetylmethylamino)-2,4,6-triiodophenyl)carbonyl)amino)-heptanoyl)amino-octadecanoic acid, methyl ester;

4-Aminobenzenebutyric acid 1,1-dimethylethyl ester;

4-Aminobenzeneheptanoic acid 1,1-dimethylethyl ester;

4-Aminobenzeneundecanoic acid 1,1-dimethylethyl ester;

4-Aminobenzenepentadecanoic acid 1,1-dimethylethyl ester; and

4-Aminobenzenenondecanoic acid 1,1-dimethylethyl ester.

6. Methyl 9/10[p-nitrobenzoylamino]octadecanoate.

7. Methyl 9/10[p-aminobenzoylamino]octadecanoate.

8. Methyl 9(10)-(7-bromoheptanoylamino)octadecanoate.

9. Methyl 9(10)-(7-azidoheptanoylamino)octadecanoate.

10. Methyl 9(10)-(7-aminoheptanoylamino) octadecanoate.

11. An x-ray contrast composition comprising a compound of formulae II or III or a pharmaceutically acceptable salt thereof,

II

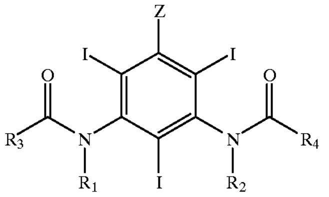

III

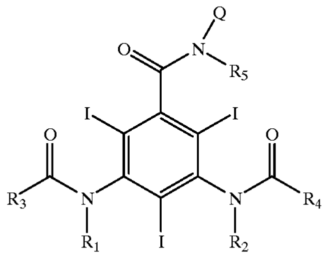

wherein

Z is

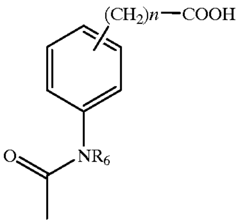

,

Q is

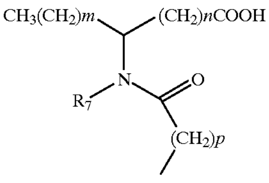

or

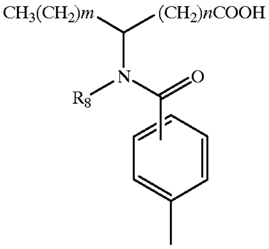

;

$R_1$, $R_5$, $R_7$ and $R_8$ are the same or different and are hydrogen, alkyl, substituted or unsubstituted cycloalkyl, substituted or unsubstituted aralkyl, substituted or unsubstituted aryl, haloalkyl, hydroxyalkyl, alkoxyalkyl, carboxyalkyl or carboxamido alkyl;

$R_2$ and $R_3$ are hydrogen;

$R_3$ and $R_4$ are methyl;

n is 2 or 3; and m and p are the same or different and are 0–24 with the proviso that m+n≦24 in a pharmaceutically acceptable vehicle.

12. The x-ray contrast composition of claim 11 wherein said cycloalkyl is substituted with at least one substituent selected from the group consisting of alkyl, halogen, hydroxy, hydroxyalkyl, alkoxy, alkanoyl, alkanoyloxy, amino, alkylamino, dialkylamino, alkanoylamino, thiol, alkylthiol, nitro, cyano, carboxy, carbamoyl, alkoxycarbonyl, alkylsulfonyl and sulfonamido.

13. The x-ray contrast composition of claim 11 wherein said aryl is phenyl, pyridyl, furanyl, thiophenyl, pyrrolyl or imidazolyl.

14. The x-ray contrast composition of claim 13 wherein said aryl is substituted with at least one moiety selected from the group consisting of halogen, nitroamino, maleimido, isothiocyanato, hydroxy, hydroxyalkyl, alkyl, alkoxy, carbamoyl, carboxamide, acylamino and carboxy.

15. The x-ray contrast composition of claim 11 wherein said compound is selected from the group consisting of:

4-(((3,5-Bis(Acetylmethylamino)-2,4,6-triiodophenyl)carbonyl)amino)benzeneacetic acid;

4-(((3,5-Bis(acetylmethylamino)-2,4,6-triiodophenyl)carbonyl)amino)benzenebutyric acid 1,1-dimethylethyl ester;

4-(((3,5-Bis(acetylmethylamino)-2,4,6-triiodophenyl)carbonyl)amino)benzenebutyric acid;

4-[[[3,5-Bis(acetylmethylamino)-2,4,6-triiodophenyl]carbonyl]amino]-benzeneheptanoic acid;

4-[[[3,5-Bis(acetylmethylamino)-2,4,6-triiodophenyl]carbonyl]amino]-benzeneheptanoic acid 1,1-dimethylethyl ester;

4-[[[3,5-Bis(acetylmethylamino)-2,4,6-triiodophenyl]carbonyl]amino]-benzeneundecanoic acid;

4-[[[3,5-Bis(acetylmethylamino)-2,4,6-triiodophenyl]carbonyl]amino]-benzeneundecanoic acid 1,1-dimethylethyl ester;

4-[[[3,5-Bis(acetylmethylamino)-2,4,6-triiodophenyl]carbonyl]amino]-benzenepenta-decanoic acid;

4-[[[3,5-Bis(acetylmethylamino)-2,4,6-triiodophenyl]carbonyl]amino]-benzenepenta-decanoic acid 1,1-dimethylethyl ester;

4-[[[3,5-Bis(acetylmethylamino)-2,4,6-triiodophenyl]carbonyl]amino]-benzene-nonadecanoic acid 1,1-dimethylethyl ester;

4-[[[3,5-Bis(acetylmethylamino)-2,4,6-triiodophenyl]carbonyl]amino]-benzene-nonadecanoic acid 9(10)-N-(4-(((3,5-Bis-(acetylmethylamino)-2,4,6-triiodophenyl)carbonyl)amino)benzoyl)amino-octadecanoic acid;

9(10)-N-(4-(((3,5-Bis-(acetylmethylamino)-2,4,6-triiodophenyl)carbonyl)amino)-benzoyl)amino-octadecanoic acid methyl ester;

9(10)-N-(7-(((3,5-Bis-(acetylmethylamino)-2,4,6-triiodophenyl)carbonyl)amino)heptanoyl)amino-octadecanoic acid; and 9(10)-N-(7-(((3,5-Bis-(acetylmethylamino)-2,4,6-triiodophenyl)carbonyl)amino)heptanoyl)amino-octadecanoic acid, methyl ester.

16. A method for medical x-ray diagnostic imaging which comprises administering to the body of a mammal a contrast effective amount of the x-ray contrast composition of claim 11.

17. The method of claim 16 wherein said administration is oral administration.

18. The method of claim 16 wherein said administration is intravenous administration.

19. The method of claim 16 wherein said medical x-ray diagnostic imaging is x-ray computed tomographic imaging.

20. A method for medical x-ray diagnostic imaging which comprises administering to the body of a mammal a contrast effective amount of the x-ray contrast composition of claim 15.

21. The method of claim 15 wherein said administration is oral administration.

22. The method of claim 15 wherein said administration is intravenous administration.

23. The method of claim 15 wherein said medical x-ray diagnostic imaging is x-ray computed tomographic imaging.

24. A process of preparing a compound of the formula

XII

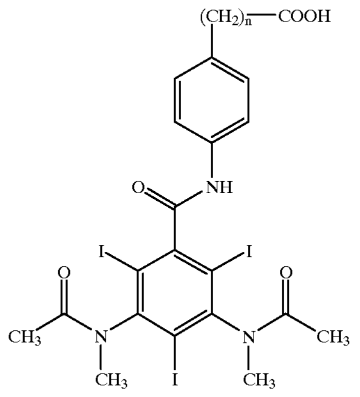

comprising the steps of:

a) reacting, in a dimethylacetamide solution, a (4-aminophenyl) alkanoic ester of the formula

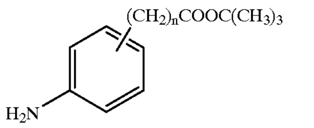

wherein n is 0–24, with N,N-dimethyldiatrizoic acid chloride of the formula

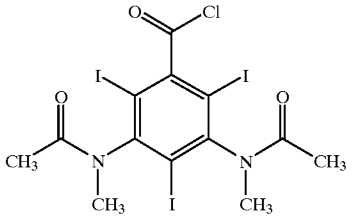

to obtain the coupled compound of the formula

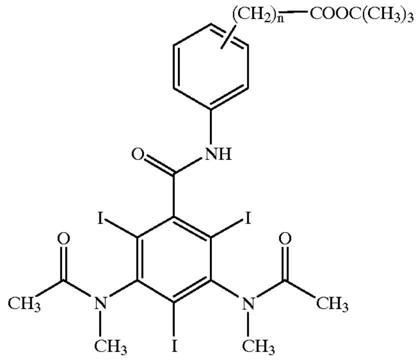

wherein n is 0–24; and b) deprotecting the coupled compound in a tetrafluoroacetate-anisole mixture.

25. A process for preparing a compound of the formula

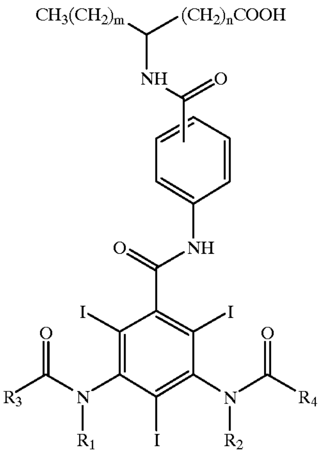

comprising the steps of:

a) hydrogenating a phenylamido compound of the formula

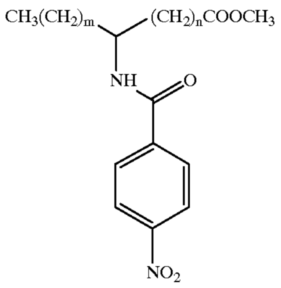

to obtain the aniline of the formula

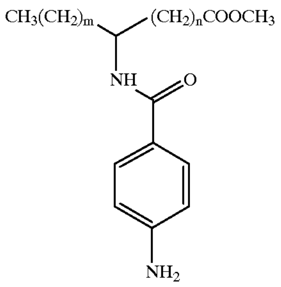

wherein m and n are independently 0–24;

$R_1$, $R_2$,$R_3$ and $R_4$ are independently hydrogen, alkyl, substituted or unsubstituted cycloalkyl, substituted or unsubstituted aralkyl, substituted or unsubstituted aryl, haloalkyl, hydroxyalkyl, alkoxyalkyl, carboxyalkyl or carboxamido alkyl;

b) condensing the aniline with N,N-dimethyldiatrizoic acid chloride of the formula

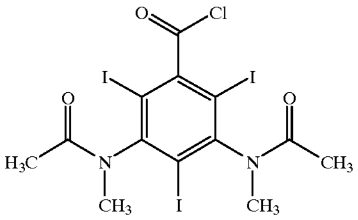

to obtain the adduct thereof; and c) hydrolyzing the adduct.

26. A process for preparing a compound of the formula

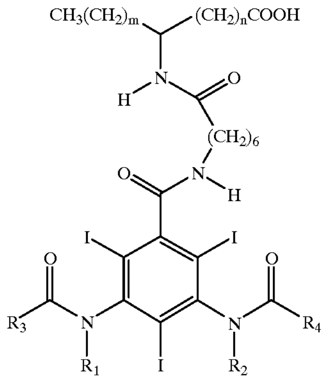

comprising the steps of:

a) treating an amide of the formula

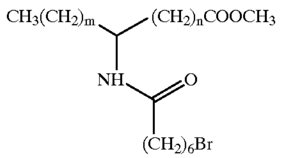

with $NaN_3$ in a dimethylformamide solution to obtain an adduct; and b) hydrogenating the adduct to obtain a compound of the formula

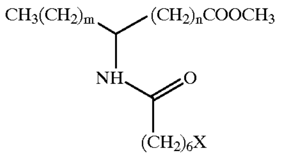

wherein m and n are independently 0–24,

X is $N_3$ or $NH_2$, and $R_1$, $R_2$,$R_3$ and $R_4$ are independently hydrogen, alkyl, substituted or unsubstituted cycloalkyl, substituted or unsubstituted aralkyl, substituted or unsubstituted aryl, haloalkyl, hydroxyalkyl, alkoxyalkyl, carboxyalkyl or carboxamido alkyl;

c) condensing the hydrogenated compound with N,N-dimethyldiatrizoic acid chloride of the formula

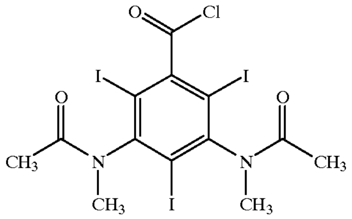

in dimethylacetamide solution to obtain an adduct; and d) hydrolyzing the adduct.

* * * * *